United States Patent
Izquierdo Alcalde

(10) Patent No.: US 8,778,405 B2
(45) Date of Patent: Jul. 15, 2014

(54) KIT OF PHARMACEUTICAL FORMULATIONS CHARACTERIZED BY THE PRESENCE OF MOLECULAR OXYGEN

(75) Inventor: David Izquierdo Alcalde, Mexico City (MX)

(73) Assignee: Comercializadora S. Car. Borr S.A. de C.V., Mexico City (MX)

( * ) Notice: Subject to any disclaimer, the term of this patent is extended or adjusted under 35 U.S.C. 154(b) by 62 days.

(21) Appl. No.: 13/104,248

(22) Filed: May 10, 2011

(65) Prior Publication Data
US 2012/0009273 A1 Jan. 12, 2012

Related U.S. Application Data

(63) Continuation-in-part of application No. PCT/MX2009/000122, filed on Nov. 13, 2009.

(30) Foreign Application Priority Data

Nov. 13, 2008 (MX) .................. MX/A/2008/014493

(51) Int. Cl.
*A01N 63/00* (2006.01)
*A61K 33/00* (2006.01)
*A61K 33/14* (2006.01)
*A61K 33/22* (2006.01)
*A61K 33/04* (2006.01)

(52) U.S. Cl.
USPC ........... 424/600; 424/661; 424/657; 424/680; 424/709; 424/93.51

(58) Field of Classification Search
None
See application file for complete search history.

(56) References Cited

U.S. PATENT DOCUMENTS

| 4,868,180 | A * | 9/1989 | Izuhara et al. ........... 514/251 |
| 6,383,534 | B1 * | 5/2002 | Dyrr et al. ........... 426/74 |
| 6,783,780 | B1 * | 8/2004 | De Jong et al. ........... 426/52 |
| 2003/0165596 | A1 | 9/2003 | Lystrup et al. |
| 2003/0232114 | A1 * | 12/2003 | Dekleva ........... 426/312 |
| 2008/0171720 | A1 * | 7/2008 | Garssen et al. ........... 514/49 |
| 2008/0199534 | A1 | 8/2008 | Goldberg et al. |
| 2009/0202678 | A1 | 8/2009 | Sampsonis et al. |

FOREIGN PATENT DOCUMENTS

CA 1339308 C 8/1997

OTHER PUBLICATIONS

Jordan, W. C., "The Effectiveness of intermittent hyperbaric oxygen in relieving drug-induced HIV-Associated neuropathy", J Natl Med Assoc. (1998), vol. 90, No. 6, pp. 355-358.*

* cited by examiner

*Primary Examiner* — Abigail Fisher
*Assistant Examiner* — Daniel L Branson
(74) *Attorney, Agent, or Firm* — Westerman, Hattori, Daniels & Adrian, LLP

(57) ABSTRACT

An array of pharmaceutical formulations characterized by the presence of molecular oxygen comprising four elements which, in combination, furnish benefits for the health of patients with HIV AIDS: (i) weight increase of the patient; (ii) increase of appetite; (iii) reduction of diarrhea; (iv) reduction of the wasting syndrome; (v) increase of stability of mood; (vi) increase of muscular mass. (vii) decrease of opportunistic diseases, in particular infections caused by *Candida*, herpes virus, cytomegalovirus, Kaposi's sarcoma; (viii) prolongation of the period wherein the patient does not require to take antiretrovirals; (ix) increase of acceptance of pharmacological treatment; x. reduction of gastritis, nausea or vomiting, headache; (xi) reduction of cases with anemia or thrombocytopenia; and (xii) a change in the phase of the disease in the patient.

6 Claims, No Drawings

KIT OF PHARMACEUTICAL FORMULATIONS CHARACTERIZED BY THE PRESENCE OF MOLECULAR OXYGEN

CROSS-REFERENCE TO RELATED APPLICATIONS

The present patent application is a continuation-in-part of International application No. PCT/MX2009/000122, filed Nov. 13, 2009, published in Spanish, which is based on, and claims priority from, Mexican Application No. MX/a/2008/014493, filed Nov. 13, 2008, both of which are incorporated herein by reference in their entireties.

BACKGROUND OF THE INVENTION

1. Field of the Invention

This invention refers to a Kit of Pharmaceutical Formulations consisting of molecular oxygen, a vitamin complex, a mineral complex, and yeast.

2. Description of Related Art Including Information Disclosed Under 37 CFR §§1.97 and 1.98

Those who are infected with HIV AIDS that take multiple vitamin compounds each day experience a slower advance in their illness, according to the periodical, "New England Journal of Medicine".

Nutritional supplements "may gain time for and allow persons with HIV to further delay the development of symptoms that require treatment with antiretroviral medications", said Lynne Mofensoon, of the National Institute of Child Health and Human Development, which financed the study.

The information originates from a study begun in Tanzania in 1995 with around 1000 pregnant women, infected with HIV AIDS and that participated in an experiment to determine if vitamin supplements could reduce transmission of the virus to the fetus.

Following this line of thought, nutritional support proper to the requirements of each patient, will provide as a result an increase in weight, correction of nutritional laboratory variables, and a consequent improvement in quality of life.

A malnourished state in the HIV AIDS patient is the principal cause which favors complications and increases morbidity of the patient. For this reason, with the invention proposed for patent, nutritional support has been achieved that helps improve the state of the patient by improving his IMC and at the same time reducing opportunistic infections.

No specialized product exists on the market that helps HIV AIDS patients to avoid malnutrition and reduce opportunistic illnesses. What we could be considered to be the closest, although not comparable, would be the product called "Prosure" of Abbot Laboratories, which is indicated for involuntary weight loss, loss of muscle mass, to improve fatigue, quality of life, and targets cancer patients.

BRIEF SUMMARY OF THE INVENTION

Glossary

In order for proper understanding, below is found a glossary with terms that are frequently used in this patent application:

Molecular Oxygen: That includes water as the solvent medium so that the oxygen and hydrogen molecule are bonded, thus its name; one of the fundamental units forming a chemical compound is the molecule, which is the smallest part of a chemical compound that takes part in a chemical reaction. In the majority of covalent compounds, the molecules consist of a group of atoms bound by covalent or coordinate bonds. Ionic compounds also do not have individual molecules, but are formed by a large number of ions having an opposite charge.

Concentrated Oxygen: this is an original formulation. In order to be orally ingested, it is diluted with an aqueous solution in order to make it suitable for consumption.

Stabilized Oxygen: state which keeps the energy of the oxygen formulation distributed in a statistical manner. A state in which the forces, influences, reactions, etc., are balanced to each other in which no change exists. This term means that the stoichiometry of the formula remains in balance, as long as no abrupt change in temperature occurs that dissipates and breaks the balance, thereby losing oxygen molecules, which in this case, is an irreversible activity.

Benefits to Health:
A) Weight increase of the patient.
B) Increase in appetite.
C) Reduction of diarrhea.
D) Reduction of the wasting syndrome.
E) Increase in mood stability.
F) Increase in muscle mass.
G) Decrease in opportunistic diseases, in particular infections caused by *Candida*, Herpes Virus, Cytomegalovirus, Kaposi's sarcoma.
H) Prolongation of the period wherein the patient does not require the administration of antiretrovirals.
I) Increase in acceptance of pharmacological treatment.
J) Reduction of gastritis, nausea, or vomiting, headache.
K) Reduction of cases with anemia or thrombocytopenia.
L) Change in the phase of the disease in the patient.

A kit of pharmaceutical formulations in accordance with the present invention is characterized by the presence of molecular oxygen comprising four elements which in combination furnish the above-defined benefits for the health of patients with HIV AIDS. The first element is a liquid element comprised of molecular oxygen, the second element is a granulated element comprised of a vitamin complex, the third element is a liquid element comprised of a mineral complex, and the fourth element is a liquid element comprised of yeast.

A method of administering the elements of the kit to provide the above-defined benefits for the health of HIV AIDS patients comprises the steps of:

A) administering an amount of 1 ml in water, three times a day, of the first element, B) administering an amount of 8 gms three times a day, of the second element, C) administering an amount of 5 ml in water, three times a day, of the third element, and D) administering an amount of 5 ml in water, three times a day, of the fourth element.

DETAILED DESCRIPTION OF THE INVENTION

Kit of Pharmaceutical Formulations comprised of four elements, molecular oxygen, vitamin complex, mineral and yeast complex, which together benefit the health of patients with HIV AIDS, such as:

a. Weight increase of the patient.
b. Increase in appetite.
c. Reduction of diarrhea.
d. Reduction of the wasting syndrome.
e. Increase in mood stability.
f. Increase in muscle mass.
g. Decrease in opportunistic diseases, in particular infections caused by *Candida*, Herpes Virus, Cytomegalovirus, Kaposi's sarcoma.

h. Prolongation of the period wherein the patient does not require the administration of antiretrovirals.

i. Increase in acceptance of pharmacological treatment.

j. Reduction of gastritis, nausea, or vomiting, headache.

k. Reduction of cases with anemia or thrombocytopenia.

l. Change in the Phase of the Disease in the Patient.

When the elements comprising the Kit act together, each of these operate upon the human organism in the most efficient form within the parameter for which they are formulated, it is notable that the efficacy of the four is more effective than if each were administered at intervals from each other.

The first of the elements that comprise the Kit is characterized by Molecular Oxygen which is assimilated by the organism via the oral route. Those who are ill with HIV AIDS have a greater need for oxygen as a nutrient and it has been demonstrated that this element is a determining factor in health.

Stabilized molecular oxygen, supplied as the first nutritional complement, rapidly acts upon the organism as it is carried through the blood stream in its molecular form and in this way, is distributed throughout all the cells wherein primary biochemical functions are performed for its benefit, in this way strengthening the immune system, by providing a greater amount of this vital element for later reaction.

This first element that is found in liquid state mainly is comprised by the Molecular Oxygen, which is an oxicompound of the halogens obtained through a synthesis process coming from hypochlorous acid and dichlorine monoxide, which later reacts with a sodium tetraphosphorus decoxide, obtaining transargononic chlorine oxide (dichlorine heptoxide. Molecular oxygen of this first element is comprised of the following:

54% Concentrated Oxygen, which is made up of 1.94% of ClNa, 1.1% of B2O3, 0.5% NaClO, 0.4% of Na2SO4, and 0.2% of NaClO3, dissolved Oxygen 10.94% and aqueous solution 38.9%, 46% bi-distilled water.

The second element comprising a Vitamin Complex in which are included: Vitamins C, E, B1, B2, Vitamin B Complex, Folic Acid, Beta Carotene, and other compounds necessary and indispensible for the human body, giving special importance to those in which HIV AIDS patients are deficient.

The second granulated element that consists of a Vitamin Complex, is made up of:

67% Muscovado Sugar
    0.01% Potassium Sorbate K
    0.01% Ascorbic Acid
    0.01% Citric Acid
    0.03% Acetylsalicylic Acid
    0.01% Folic Acid
    0.01% Vitamin A Vitamin A Palmitate
    0.01% Vitamin E Alpha tocopherol succinate
    0.01% Vitamin B1 Thiamine
    0.01% Vitamin B2
    0.01% Vitamin B3
    0.02% Vitamin B6 Pyridoxine
    0.01% Vitamin B12 Cyanocobalamin
    0.01% Beta Carotene
    13.4% Nutrifort, of which:
        0.001% Phenylalanine
        0.001% Isoleucine
        0.001% Leucine
        0.001% Lysine
        0.001% Methionine
        0.001% Threonine
        0.001% Tryptophan
        0.001% Valine
        0.001% Glycine
        0.001% Glutamic Acid
        0.001% Alanine
        0.0001% Aspartic Acid
        0.0001% Histidine
        0.0001% Proline
        0.0001% Tyrosine
        0.0001% Arginine
        0.0001% Cysteine
        0.0001% Serine
    0.04% Sodium Chlorine Salt
    0.01% Zinc Sulfate
    0.03% L-Lysine The third element that consists of a Mineral Complex, within which they form part; Calcium, Iron, Cobalt, Molybdenum Sulfur, Magnesium, Potassium, Iodine, among others, all supplied in a solid base which is easily assimilated by the organism.

The role of calcium in the blood, for example, involves neuromuscular excitability and coagulation of the blood. Ions act upon a certain group of enzymes and the role of electrolytes is vital in regulating the acid base balance in the cell. Normal ossification requires a normal relationship between potassium and calcium in the extracellular fluid, and must be maintained in order to ensure normal muscle activity.

The third liquid element that consists of a Vitamin Complex, is made up of:

99.9% Bi-Distilled Water
    0.006% Prepared Oxygen
    0.002% Citric Acid
    0.003% Concentrated Flavor
    3% Sodium Phosphate
    2% Sodium Nitrate
    5% Potassium Chloride
    4.5% Magnesium Sulfate
    0.2% Iron Oxide
    0.01% Sulfur Oxide
    0.01% Cobalt Hydroxide
    0.02% Molybdenum Oxide
    0.03% Iodine Oxide The fourth element that consists of a hydroalcohol extract from unfermented yeast cells, separated by precipitation of barium sulfate. With this complement the pantothenic acid, biotin, and aneurin are elevated and, combined they form a complete polysaccharide that gives protective support to tissues, cartilages, the cornea, and the mucosa, among others.

The fourth liquid element characterized by yeast, is made up of:

98.6% Water
    0.008% Acetic Acid diluted at 5% acidity
    0.003% Phosphoric Acid 85% USP
    0.0001% Sodium Benzoate
    0.013% *Saccharomyces Cerevisiae* Yeast
    0.003% Prepared Oxygen, which is a dissolution of concentrated molecular oxygen The innovative quality of the Pharmaceutical Compound lies in the Oxygen, because there is no such nutritional supplement with oxygen as yet which allows the human organism to obtain greater energy due to the fact that cells act as fuel in the presence of oxygen and carbon bioxide favoring biochemical conditions for greater attainment of energy.

It is also know that carriers of HIV-AIDS have a greater need for oxygen as a nutrient. When there is a deficiency thereof, it can stimulate almost all degenerative illnesses in the organism.

Once it is furnished to the organism it rapidly acts as it is carried through the blood stream in its molecular form and in this way, is distributed throughout all the cells wherein primary biochemical functions are performed for its benefit, in this way strengthening the immune system, by providing a greater amount of this vital element.

The capacity of the body to fight the HIV virus depends absolutely on an efficient immune system as well as depending in great part on a high supply, which is continuous and pure, of oxygen. It has been shown that stabilized oxygen supplied to the body, strengthens the immune system, especially against neoplasia.

The main difference from other products is the presence of oxygen which is assimilable by the body by oral route, that allows the body to modify oxide reduction reactions, improving its concentration within the tissues and increasing anaerobic concentrations that prevent the development of viral infections. They reduce the production of free radicals that have to do with tissue damage.

EXAMPLES

The following examples are given in order to illustrate the invention but are not to be considered limitative at any time.

The use of proper nutritional support, together with anti-retroviral therapy, tends to give an early stabilization response to the illness and consequently, improves the quality of life of the patient.

If the Pharmaceutical Compounds are consumed as nutritional support, it offers great benefit to patients, and is administered in the following form:
 a. The amount of 1 ml in water, three times a day, of the first liquid element characterized by the molecular oxygen.
 b. The amount of 8 gms, three times a day, of the second granulated element characterized by the Vitamin Complex.
 c. The amount of 5 ml, three times a day, of the third liquid element characterized by the Mineral Complex.
 d. The amount of 5 ml, three times a day, of the fourth liquid element characterized by the Yeast.

The invention claimed is:

1. A kit of pharmaceutical formulations comprising four elements which in combination furnish benefits for the health of patients with HIV AIDS wherein:
 the first element comprises 1.94% of NaCl, 1.1% of B2O3, 0.5% of NaClO, 0.4% of Na2SO4, and 0.2% of NaClO3, 10.94% dissolved Oxygen, 38.9% aqueous solution, and 46% bi-distilled water;
 the second element is a granulated element comprising a vitamin complex;
 the third element is a liquid element comprising a mineral complex; and
 the fourth element is a liquid element comprising yeast.

2. The kit of pharmaceutical formulations in accordance with claim 1, wherein the second element comprises a vitamin complex which contains:
 67% Muscovado Sugar;
 0.01% Potassium Sorbate K;
 0.01% Ascorbic Acid;
 0.01% Citric Acid;
 0.03% Acetylsalicylic Acid;
 0.01% Folic Acid;
 0.01% Vitamin A;
 0.01% Vitamin E;
 0.01% Vitamin B1;
 0.01% Vitamin B2;
 0.01% Vitamin B3;
 0.02% Vitamin B6;
 0.01% Vitamin B12;
 0.01% Beta Carotene;
 0.04% Sodium Chloride Salt;
 0.01% Zinc Sulfate;
 0.03% L-Lysine; and
 13.4% of a composition which contains:
  0.001% Phenylalanine,
  0.001% Isoleucine,
  0.001% Leucine,
  0.001% Lysinate,
  0.001% Methionine,
  0.001% Threonine,
  0.001% Tryptophan,
  0.001% Valine,
  0.001% Glycine,
  0.001% Glutamic Acid,
  0.001% Alanine,
  0.0001% Aspartic Acid,
  0.0001% Histidine,
  0.0001% Proline,
  0.0001% Tyrosine,
  0.0001% Arginine,
  0.0001% Cysteine, and
  0.0001% Serine.

3. The kit of pharmaceutical formulations in accordance with claim 1, wherein the third element comprises a mineral complex which contains:
 99.9% Bi-Distilled Water;
 0.006% Prepared Oxygen;
 0.002% Citric Acid; and
 0.003% Flavor.

4. The kit of pharmaceutical formulations in accordance with claim 1, wherein the fourth element comprises yeast, and contains:
 98.6% Water;
 0.008% Acetic Acid diluted at 5% acidity;
 0.003% Phosphoric Acid 85% USP;
 0.0001% Sodium Benzoate;
 0.013% Saccharomyces Cerevisiae; and
 0.003% Prepared Oxygen.

5. The kit of pharmaceutical formulations in accordance with claim 2, wherein the Vitamin A, Vitamin E, Vitamin B1, Vitamin B6 and Vitamin B12 of the vitamin complex are respectively retinyl palmitate, alpha tocopherol succinate, thiamine, pyridoxine and cyanocobalamin.

6. A method of administering the four elements of the kit of pharmaceutical formulations in accordance with claim 1, to provide benefits for the health of HIV AIDS patients, wherein the first element is a liquid element comprising a concentrated oxygen formulation, the second element is a granulated element comprising a vitamin complex, the third element is a liquid element comprising a mineral complex, and the fourth element is a liquid element comprising yeast, the method comprising the steps of:
 A) administering an amount of 1 ml in water, three times a day, of the first element;
 B) administering an amount of 8 gms three times a day, of the second element;
 C) administering an amount of 5 ml in water, three times a day, of the third element; and
 D) administering an amount of 5 ml in water, three times a day, of the fourth element.

* * * * *